(12) United States Patent
Weinberg et al.

(10) Patent No.: US 7,402,425 B2
(45) Date of Patent: Jul. 22, 2008

(54) STRESS-BASED ELECTROSTATIC MONITORING OF CHEMICAL REACTIONS AND BINDING

(75) Inventors: Marc S. Weinberg, Needham, MA (US); Jeffrey Borenstein, Holliston, MA (US); Christopher E. Dubé, Lexington, MA (US); Ralph Hopkins, Chestnut Hill, MA (US); Edwin Carlen, Cambridge, MA (US)

(73) Assignee: The Charles Stark Draper Laboratory, Inc., Cambridge, MA (US)

( * ) Notice: Subject to any disclaimer, the term of this patent is extended or adjusted under 35 U.S.C. 154(b) by 312 days.

(21) Appl. No.: 10/791,108

(22) Filed: Mar. 2, 2004

(65) Prior Publication Data
US 2005/0196877 A1   Sep. 8, 2005

(51) Int. Cl.
*C12M 1/34* (2006.01)
(52) U.S. Cl. ............ 435/287.2; 435/7.1; 435/283.1; 73/861.47; 73/262; 73/263; 73/269; 73/279; 436/149; 436/806; 204/282; 422/50; 422/82.01; 422/82.02; 422/61; 422/68.1
(58) Field of Classification Search ............ 422/50, 422/82.01, 82.02, 61, 68.1; 436/149, 806; 73/861.47, 262, 263, 269, 279, 715, 718; 204/282; 435/7.1, 283.1, 287.2
See application file for complete search history.

(56) References Cited

U.S. PATENT DOCUMENTS

| | | | |
|---|---|---|---|
| 5,050,035 A | 9/1991 | Hegner et al. | |
| 5,262,127 A | 11/1993 | Wise et al. | |
| 5,308,649 A * | 5/1994 | Babacz | 427/562 |
| 5,339,051 A | 8/1994 | Koehler et al. | |
| 5,698,089 A | 12/1997 | Lewis et al. | |
| 6,114,658 A | 9/2000 | Roth et al. | |
| 6,167,748 B1 | 1/2001 | Britton, Jr. et al. | |
| 6,673,533 B1 * | 1/2004 | Wohlstadter et al. | 435/6 |
| 7,086,288 B2 | 8/2006 | Lee et al. | |
| 2003/0019299 A1 | 1/2003 | Horie et al. | 73/718 |
| 2003/0027351 A1 | 2/2003 | Manalis et al. | 436/165 |
| 2003/0186228 A1 | 10/2003 | McDevitt et al. | 435/6 |
| 2003/0233882 A1 | 12/2003 | Mei | 73/718 |

(Continued)

FOREIGN PATENT DOCUMENTS

EP        0 990 885        4/2000

(Continued)

OTHER PUBLICATIONS

Baselt, D.R. et al., "Design and Performance of a microcantilever-based hydrogen sensor," *Sensors and Actuators B.*, Elsevier Sequoia S.A., Lausanne, CH., vol. 88, No. 2, pp. 120-131 (2003).

(Continued)

*Primary Examiner*—Long V. Le
*Assistant Examiner*—Melanie J Yu
(74) *Attorney, Agent, or Firm*—Goodwin Procter LLP

(57) ABSTRACT

Electrostatic capacitance measurements are used to detect chemical or biological analytes, or chemical interactions, with great sensitivity. A diaphragm is coated with a material capable of selectively interacting with an analyte of interest, and interaction of the analyte with the coating exerts stresses tangential to the diaphragm's surface. These stresses cause diaphragm displacements that are sensed as varying capacitance.

19 Claims, 8 Drawing Sheets

U.S. PATENT DOCUMENTS

2004/0096357 A1* 5/2004 Majumdar et al. ............ 422/57

FOREIGN PATENT DOCUMENTS

EP       1 306 449       5/2003
WO      WO 01/71336      9/2001

OTHER PUBLICATIONS

Chatzandroulis, S., "Fabrication of single crystal Si cantilevers using a dry release process and application in a capacitive-type humidity sensor", *Microelectronic Engineering, Elsevier Publishers BV., Amsterdam NL*, vol. 61-62, pp. 955-961 (2002).

Pepper, J. et al., "Detection of proteins and intact microorganisms using microfabricated flexural plate silicon resonator arrays", *Sensors and Actuators B., Elsevior Sequoia A.S., Lausanne, CH.*, vol. 96, No. 3, pp. 565-575 (2003).

International Search Report for International Application No. PCT/US2005/006680 dated Jun. 13, 2005.

* cited by examiner

STRESS-BASED ELECTROSTATIC MONITORING OF CHEMICAL REACTIONS AND BINDING

FIELD OF THE INVENTION

The present invention relates to measurement instruments, and in particular to instruments for measuring analyte binding and the progress of chemical reactions.

BACKGROUND OF THE INVENTION

The presence and concentration of analytes, as well as the progress and efficiency of chemical reactions, are typically measured directly—e.g., through optical monitoring if a reaction produces an observable change in light-absorption characteristics, or indirectly—e.g., by changes in mass or volume. Many of the methods typically employed require attachment of a label compound whose properties (i.e., fluorescent, radioactive, chemiluminescent, or absorbing) enable sensitive detection. These methods, however, require development of label reagents, add steps to the detection process, and modify the analyte. In the absence of label compounds, conventional measurements operate on a gross scale, and as a result require substantial amounts of analyte.

Enhanced sensitivity has recently been achieved using small micromachined cantilevers and flexural plate wave (FPW) sensors to facilitate monitoring chemical reactions and interactions on a microscopic scale. In the cantilever, the reaction is transduced into mechanical stresses. These stresses are detected with a high degree of sensitivity. Cantilever arrangements can be difficult to manufacture and operate due to the small size and fragility of the fingers, however, and to the need to separate analytes from the readout mechanism. Because the cantilevers are delicate, applying selective coatings can be difficult. To separate the analytes from readout electronics, optical readouts usually employing reflection may be employed. Cantilever-based approaches have achieved success primarily in specialized laboratories with personnel trained to handle the nuances of such devices.

FPW systems may utilize a diaphragm that is acoustically excited by interdigitated fingers to establish a standing wave pattern. The diaphragm is coated with the selective material, and interaction of analytes with the coating increases the effective thickness of the diaphragm, thereby affecting the frequency of the standing wave so as to indicate the degree of interaction. Because these devices are constructed of conducting, mechanical, and piezoelectric layers, bimetallic effects can produce unwanted temperature sensitivity. To reduce thermal distortions, FPW sensors are typically run at high resonant frequencies. Unfortunately, the high operating frequency itself limits sensitivity (in addition to requiring somewhat complex electronics).

BRIEF SUMMARY OF THE INVENTION

The present invention overcomes these problems by using electrostatic capacitance measurements to detect desired chemical or biological analytes, or chemical interactions, with great sensitivity. A diaphragm is coated with a material capable of selectively interacting with an analyte of interest, and interaction of the analyte with the coating exerts stresses tangential to the diaphragm's surface. These stresses cause diaphragm displacements that are sensed as varying capacitance between the diaphragm, which includes or consists of a conductive material and thereby serves as an electrode, and a counter electrode mounted in opposition to the diaphragm. The diaphragm is preferably a single material, such as boron-doped silicon, to reduce or eliminate thermally induced deflections. Binding results in stresses that deflect the diaphragm and change in the size of the gap between the diaphragm and the counter electrode.

The coating may, for example, include polypeptides (e.g., antibodies), nucleic acids, or other biomolecules that interact with free analytes of interest. More generally, however, the invention is amenable to use in connection with any molecular species susceptible to capture and binding as described below.

Accordingly, in a first aspect, the invention features a sensor comprising a diaphragm including a conductive portion and a selective coating on one face, and a counter electrode spaced from and in opposition to the diaphragm. Interaction of the selective coating with an analyte deforms the diaphragm, thereby altering the capacitance of the sensor so as to indicate a degree of interaction (i.e., binding and/or chemical reaction).

Unlike cantilever-based approaches, the diaphragm of the present invention can be configured to separate and protect the electrode gap from the analyte flow. The counter electrode may be micromachined at the wafer level, resulting in a more compact, inexpensive, and rugged design. A single-material diaphragm offers enhanced sensitivity and reduced thermal susceptibility relative to typical FPW devices.

To maximize sensitivity, the selective coating may cover only a portion of the face of the diaphragm, for example, its central half or the outer portion. Because deflection of the diaphragm is sensitive to a pressure differential, the pressure is desirably equalized on both sides of the diaphragm. For example, pressure may be equalized through the use of perforations through the counter electrode and/or a pressure relief channel or hole between opposing faces of the diaphragm.

In some embodiments, the entire diaphragm is conductive (e.g., silicon), whereas in other embodiments, the diaphragm comprises a conductive overcoat. The selective coating may, for example, comprise a polypeptide (e.g., an antibody or an enzyme) or an antigen.

In a second aspect, the invention features a method of detecting binding to or reaction with a selective material. The method utilizes a sensor comprising a diaphragm including a conductive portion, a selective coating on one face of the diaphragm, and a counter electrode spaced from and in opposition to the diaphragm. Interaction of the selective coating with an analyte deforms the diaphragm, thereby altering the capacitance of the sensor. The method therefore comprises measuring the capacitance of the sensor to determine the degree of interaction between the analyte and the selective coating.

In some embodiments, the measurement step comprises comparing the sensor capacitance to a reference capacitance. For example, the reference capacitance may be equal to a capacitance of the sensor in the absence of interaction with the selective coating.

The method may further comprise the step of exposing at least the selective coating to a fluid; the measurement step indicates whether an analyte that binds to the coating is present in the fluid. The fluid may comprise a gas or a liquid. The deformation may be proportional to binding energy, which indicates a degree of binding.

Because the invention is suitable for silicon micromachining and because of the ability to achieve small device sizes, deployments in arrays are both feasible and desirable. Arrays offer both redundancy and the ability to utilize a number of selective coatings to enhance differentiation and quantitative measurement.

BRIEF DESCRIPTION OF THE DRAWINGS

The foregoing discussion will be understood more readily from the following detailed description of the invention, when taken in conjunction with the accompanying drawings, in which.

The various elements may not be drawn to scale.

DETAILED DESCRIPTION OF THE PREFERRED EMBODIMENT

Figure 1:
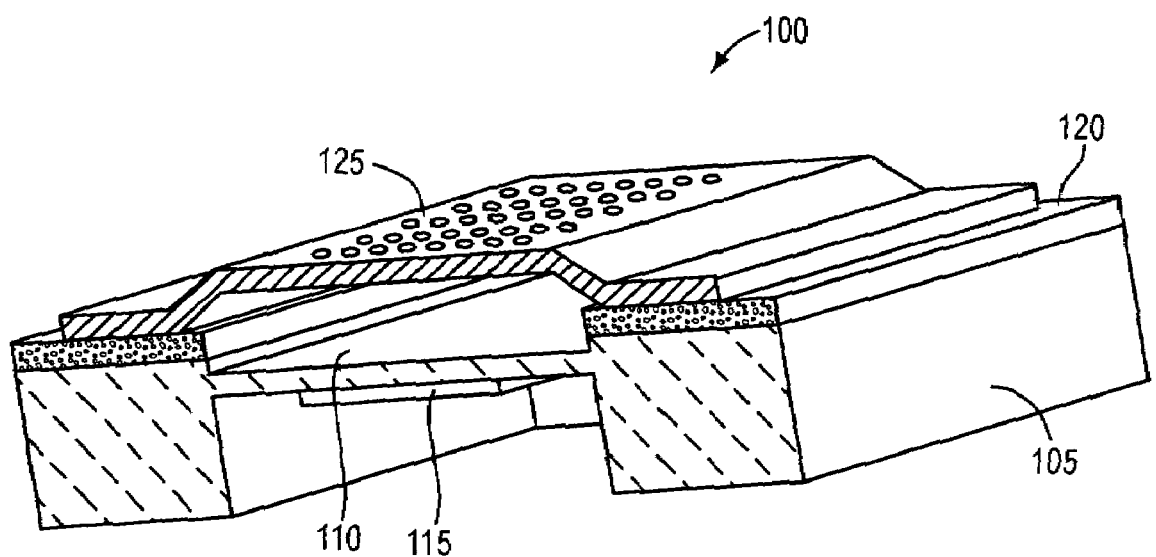
FIG. 1 is a perspective sectional view of a sensor in accordance with the present invention.

With reference to FIG. 1, a representative measurement device 100 in accordance with the invention comprises a fixture or substrate 105, which secures the edges of a conductive diaphragm 110. The diaphragm may be circular, rectangular (as illustrated), or other shape. (As used herein, the term "conductive" means electrically conductive or semiconductive, as those terms are understood in the art.) A selective coating 115, described in greater detail below, is applied to the bottom face of diaphragm 110. Since the diaphragm 110 and its support by the substrate 105 are continuous, coating 115 resides within a cavity formed by the substrate.

An insulating layer 120 (e.g., a coating of rubber or plastic, or an oxide) is provided on a top surface of substrate 105. A counter electrode 125 is secured to the insulating layer 120 in opposition to diaphragm 110, thereby forming a gap between the diaphragm and the counter electrode.

It is generally important to maintain equal pressure on both sides of diaphragm 110 during operation. One or more of several approaches may be followed in this regard. As illustrated in FIG. 1, counter electrode 125 may be perforated. Moreover, substrate 105 may include one or more apertures or valves; desirably, these are placed outside the coating and diaphragm area where they will not interfere with deflection. Alternatively, diaphragm 110 may not be attached to the substrate on all sides. The resulting gap between substrate 105 and a portion of diaphragm 110 serves to equalize pressure on both sides of the diaphragm.

Diaphragm 110 can be formed of any conductive material (e.g., a metal, a pigment-loaded polymer, or a semiconductor), but that material must be capable of withstanding repeated stresses at a thickness level small enough to undergo measurable deformations as a result of analyte interactions with coating 115. Moreover, it is preferred that diaphragm 110 be compositionally uniform throughout its extent, since, for example, diaphragms having multiple layers with different thermal-response properties will produce thermal distortion. The structure 100 can be fabricated in many ways, e.g., by micromachining or by conventional silicon-processing techniques. For example, diaphgram 110 and substrate 115 may be created from standard six-inch silicon wafers using masking and reactive-ion etching techniques. Conventional oxidation and masking can be used to form insulating layer 120. A representative device may be, for example, 500 µm long, 1000 µm wide, and 1.5 µm thick.

Selective coating 115 may comprise a chemical moiety that binds to an analyte of interest. The moiety may be or reside on a polymer, nucleic acid, a polypeptide, a protein nucleic acid, a substrate interactive with a polypeptide (e.g., an enzyme), an enzyme interactive with a substrate, an antibody interactive with an antigen, an antigen interactive with one or more antibodies, or other biomolecule.

Most simply, the measurement device 100 can be used to detect the presence of an analyte of interest in a candidate solution to which selective coating 115 is exposed. If stress above a noise threshold is observed, the presence of the analyte in the candidate solution is confirmed. More elaborate measurements can provide further information, e.g., an estimate of the concentration of the analyte. This may be accomplished by monitoring the extent of binding over time, and generally requires some empirically predetermined relationships between concentration and binding behavior. Less than complete equilibrium saturation of coating 115, for example, as reflected by a final reading below the maximum obtainable under full saturation conditions, may offer a direct indication of concentration. If saturation is reached, the time required to achieve this condition, or the time-stress profile (i.e., the change in observed stress over time) may indicate concentration—again, typically, by comparison with reference profiles previously observed for known concentrations.

Figure 2:
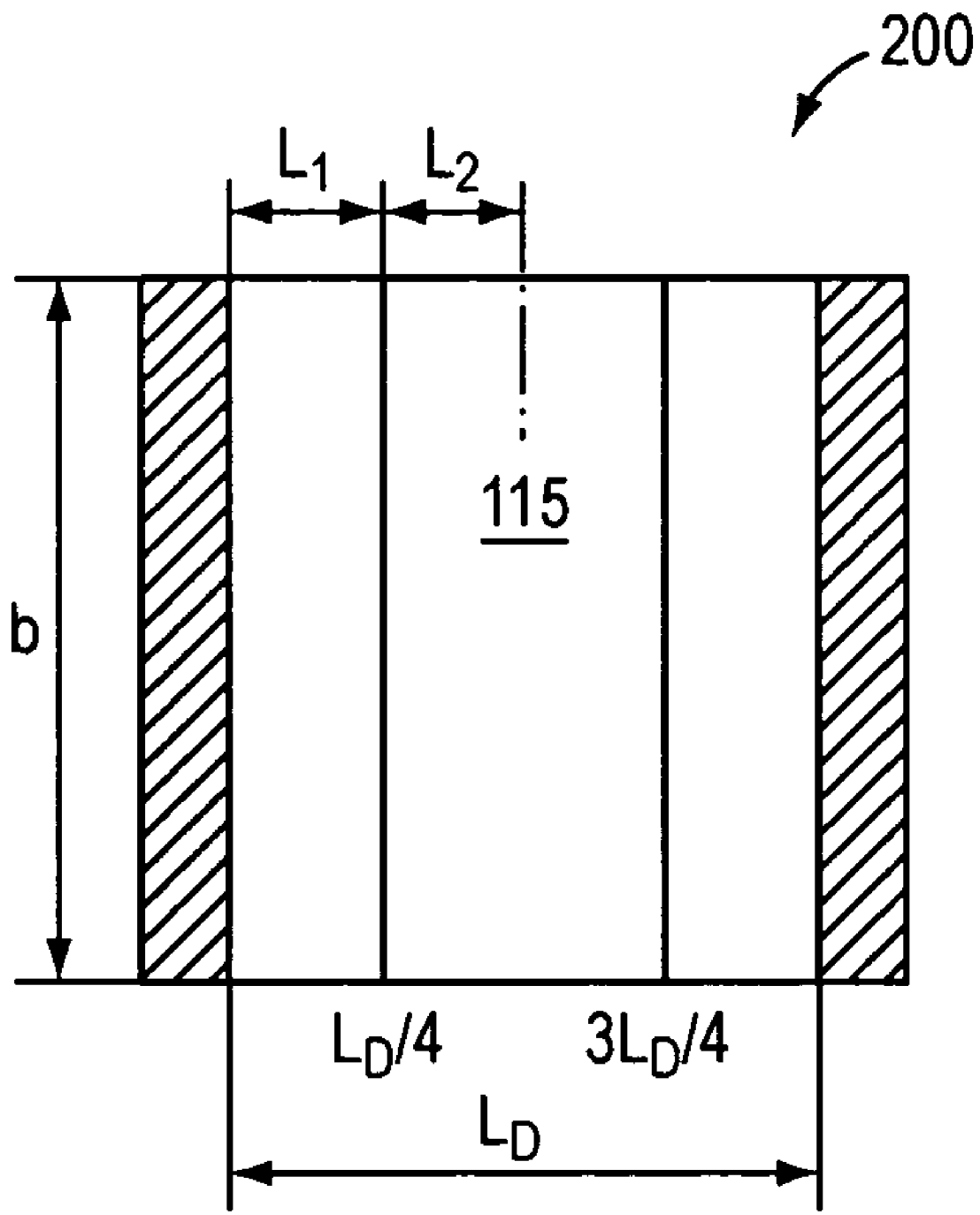
FIG. 2 is a plan view of a coated diaphragm in accordance with the present invention.

At the same time, knowledge of the dynamics of diaphragm behavior can facilitate a priori measurements even in the absence of reference data. Such knowledge can also dictate design of the device. With reference to FIG. 2, an exemplary approach utilizes a rectangular diaphragm 200 whose length $L_D$ is less than half its width b (i.e., $b>2L_D$), and which is secured along all edges. Because the width is sufficiently greather than the length, this configuration can be accurately modeled as a simple beam. Assume that the diaphragm is made of an elastic material such as silicon of thickness $h_{Si}$. The coating 115 has a uniform thickness $h_c$, covers 50% of the area of diaphragm 200 and extends from $L_D/4$ to $3L_D/4$. Binding of an analyte to coating 115 exerts a compressive or tensile stress on the silicon diaphragm 200. Although the stress is probably biaxial, the ensuing beam anaylsis considers only the lengthwise stress that deflects the diaphragm.

A reasonable estimate of the Young's modulus of coating 115 is 1% that of silicon (hereafter $Y_{Si}$), a value typifying many polymers. As an upper limit on stress, it is assumed that the film can shrink 1% if not restrained; consequently, the stress available for deforming the diaphragm is $10^{-4} Y_{Si}$.

Figure 3:
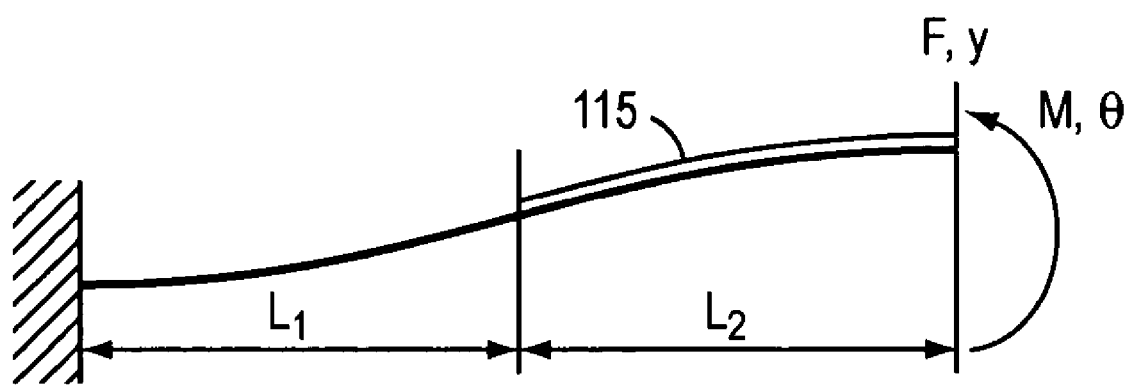
FIG. 3 graphically depicts the bending behavior of the diaphragm shown in FIG. 2.
Figure 4:
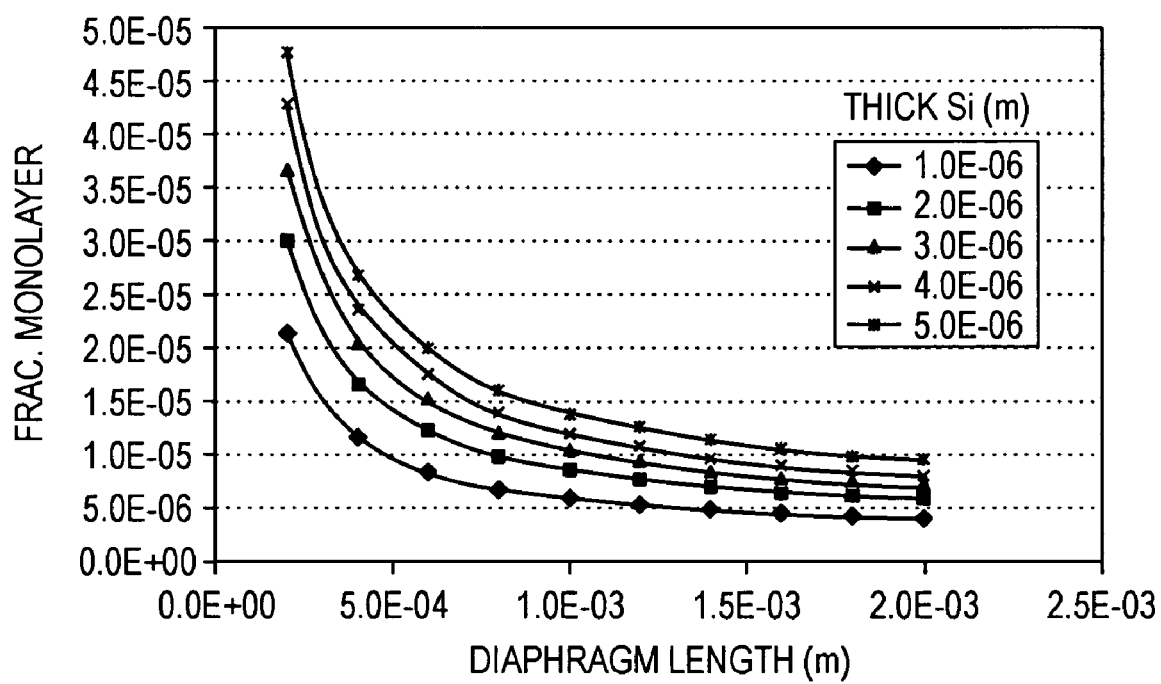
FIG. 4 graphically depicts the resolvable fraction of an analyte molecular layer versus diaphragm length and thickness.
Figure 5:
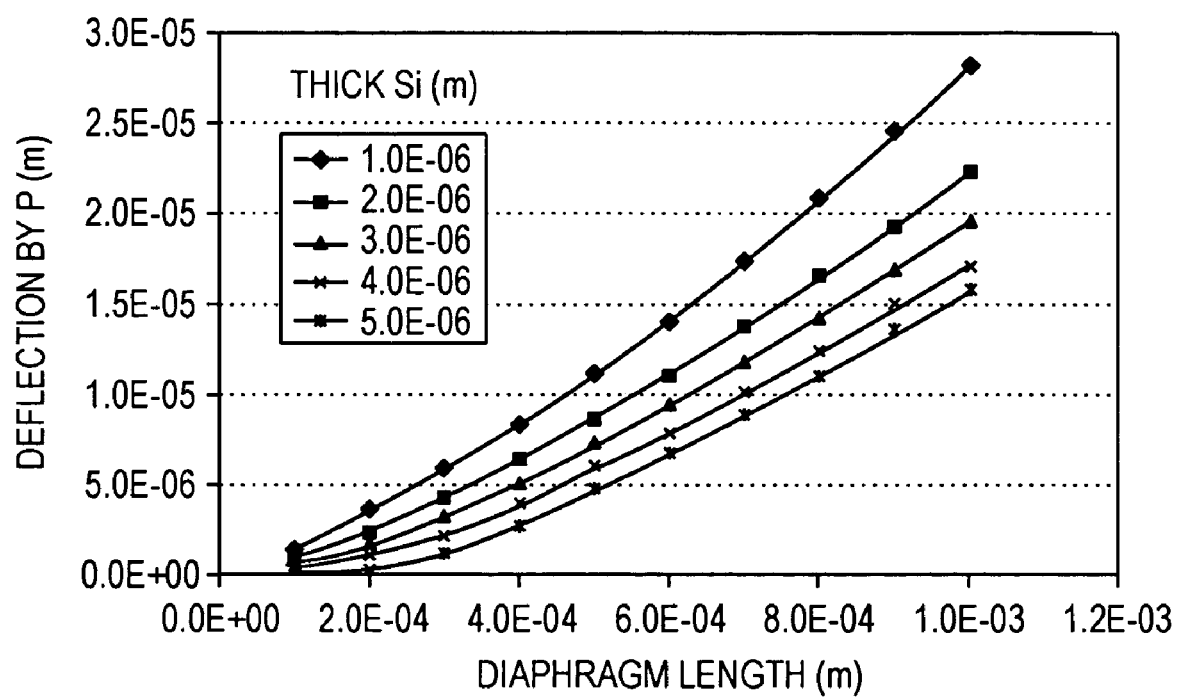
FIG. 5 graphically depicts the relationship of maximum deflection from baseline due to 1 atmosphere pressure across a diaphragm versus diaphragm length and thickness.
Figure 6:
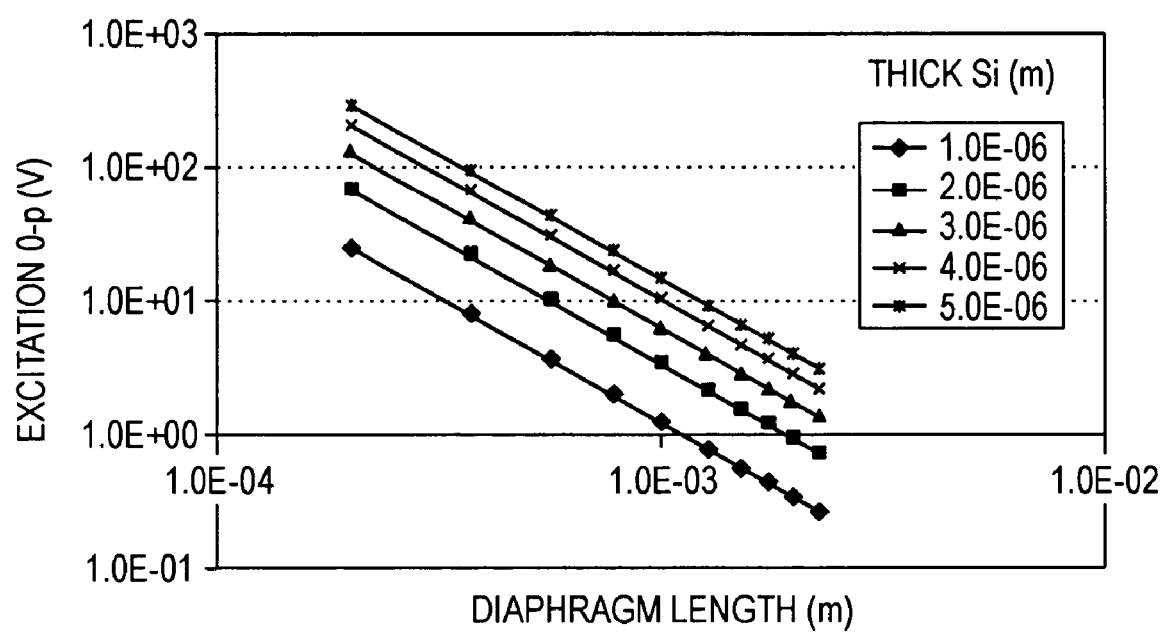
FIG. 6 graphically depicts excitation voltage as limited by snap-down versus diaphragm length and thickness.
Figure 7:
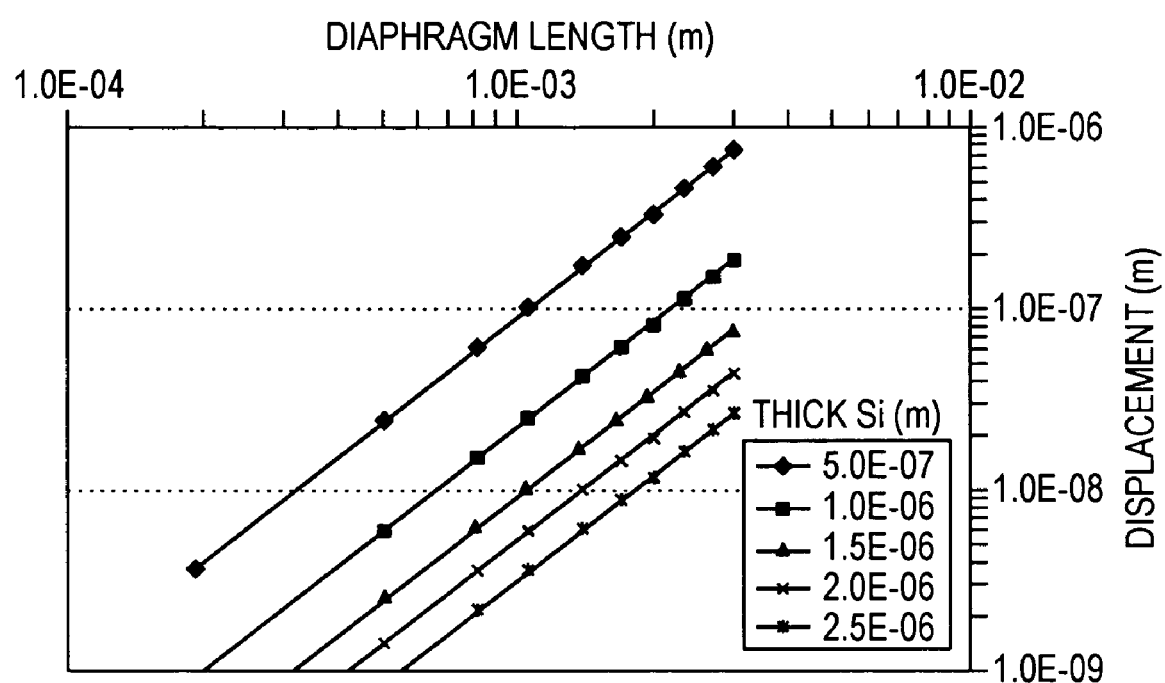
FIG. 7 graphically depicts deflection caused by a single analyte layer versus diaphragm length thickness.

The axial adhesion axial force is modeled as a torque couple applied at $x=L_D/4$ and $x=3L_D/4$. The torque magnitude is:

$$M = \epsilon_c Y_c b h_c (y_c - y_{om}) \qquad \text{Eq. 1}$$

where $Y_c$=coating Young's modulus ($1.68 \times 10^{-9}$ N/m$^2$); $\epsilon_c$=unrestrained strain (0.01); b=width of diaphragm 200 (the coating 115 traverses the entire width b); $h_c$=thickness of coating plus analyte ($10^{-9}$ m, one monolayer coating and one of analyte); and $y_c-Y_{om}$=vertical distance between coating's center and the neutral axis for torque inputs when a pure torque is applied With the coating covering the central portion of the plates ($L_1=L_2$ in FIG. 2), the maximum deflection is:

$$y_{cen} = \frac{ML_D^2}{8R_M} \quad \text{Eq. 2}$$

where $L_D$=diaphragm length (assumed less than 50% b) and $R_M$=radius of curvature for unit torque (the sum of the YI terms where the inertia products I are calculated about the torque neutral axis). This is illustrated in FIG. 3. The point force required to deflect the diaphragm center is given by:

$$F_{cen} = k_{cen}y_{cen} = \frac{192R_M}{L_D^3}y_{cen} \quad \text{Eq. 3}$$

The deflections and strains of diaphragm 110 in response to varying loads are straightforwardly determined (indeed, published tables can be employed; see, e.g., R. J. Roark and W. Young, *Formulas for Stress and Strain*, McGraw-Hill (5th ed. 1975), page 408). Among several cases, values may be tabulated for held and fixed edges where the larger dimension is 1.5 times the smaller dimension. For this situation, the plate can be modeled as very wide (the plane strain assumption) so that the low-pressure results can be compared to tabulated closed-form solutions.

Figure 8:
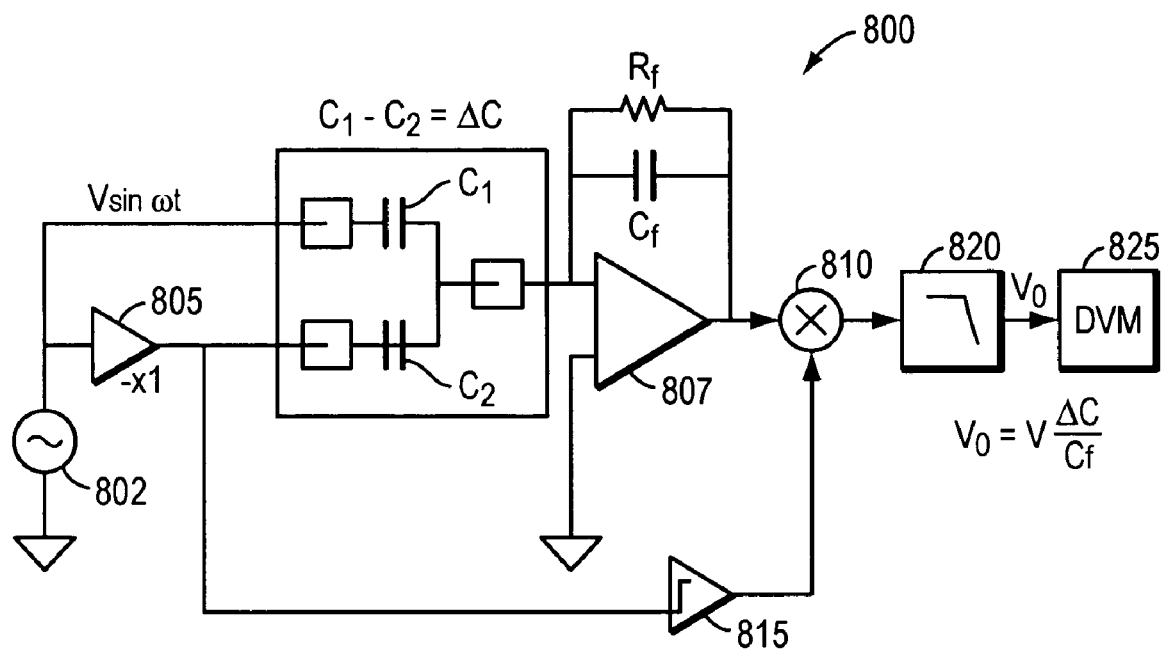
FIG. 8 schematically depicts a detection circuit useful in conjunction with the invention.

A representative circuit 800 suitable for use in connection with the present invention and offering precise capacitance measurements is shown in FIG. 8. The circuit includes two measurement devices 100, each having an identical baseline capacitance and indicated at $C_1$, $C_2$. The capacitance of a single measurement device 100 is given by:

$$C_s = \frac{\varepsilon b L_D F_{sd}}{g_s} \quad \text{Eq. 4}$$

where $\varepsilon$=permittivity of free space ($8.85\times10^{-12}$ F/m), $g_s$=capacitor air gap (3 μm), and $F_{sd}$=bridge construction factor (50%). For efficient design, the counter electrode should not be built over the diaphragm portion that does not deflect vertically.

In operation, the measurement devices $C_1$, $C_2$ are identical but only one (e.g., $C_1$) is exposed to a candidate fluid. The other ($C_2$) is used as a baseline reference, and desirably experiences the same thermal environment as $C_1$. Alternatively, the reference device may lack a selective coating, in which case it, too, may be exposed to the candidate fluid. One "plate" (i.e., the diaphragm) of measurement device $C_1$ receives a time-varying voltage signal $V\sin\omega t$ from an AC source 802, and the same plate of measurement device $C_2$ receives an inverted form of the same signal via an inverter 805. The other plates (i.e., the counter electrodes) of measurement devices $C_1$, $C_2$ are connected together and to the inverting input terminal of an operational amplifier 807. Accordingly, if the capacitances of $C_1$, $C_2$ were identical, the resulting voltage would be zero due to inverter 805.

Operational amplifier 807 is connected in a negative feedback circuit. The non-inverting terminal is at ground potential, so the output voltage is proportional to the voltage difference $\Delta C = C_1 - C_2$. A feedback resistor $R_f$ and a feedback capacitor $C_f$ bridge the inverting input terminal and the output terminal of the amplifier 807. The output of amplifier 807 is fed to an input terminal of a voltage multiplier 810. The other input terminal of multiplier 810 receives the output of a device 815, such as a Schmitt trigger, that that produces a rectangular output from the sinusoidal signal provided by inverter 805. When configured in this fashion, multiplier 810 acts to demodulate the signal from amplifier 807, and a low pass filter 820 extracts the DC component from the demodulated signal. The voltage read by the digital voltmeter (DVM) 825 is therefore $$V_O = V_{\text{rms}}\frac{\Delta C}{C_f}.$$

DVM 825 ordinarily includes a display and is desirably programmable, so that the received voltage may converted into a meaningful reading. Most simply, DVM 825 allows the user to specify a threshold, and if the sensed voltage exceeds the threshold, DVM 825 indicates binding of the analyte of interest to coating 115. More elaborately, DVM 825 monitors and stores the voltage as it evolves over time, and includes a database relating voltage levels and their time variations to concentration levels that may be reported.

Noting that both an active and reference capacitor are attached to the amplifier inputs, the minimum detectable diaphragm rms position signal is determined by:

$$g_{res} = g_s\frac{V_N}{V_x}\frac{(2C_s + C_N + C_{fb})}{C_s}\sqrt{2f_{band}} \quad \text{Eq. 5}$$

where $V_N$=preamplifier input voltage noise (6 nV/$\sqrt{\text{Hz}}$), $V_x$=excitation voltage specified as zero to peak, $f_{band}$=frequency bandwidth over which measurement is taken (1 Hz), $C_{fb}$=feedback capacitance (2 pF), and $C_N$=additional capacitance attached to preamplifier input node (3 pF). The factor of two under the square root involves the conversion of zero to peak voltages to rms uncertainty. Dividing $g_{res}$ by the deflection for a monolayer determines the fraction of a layer that can be resolved. The O-p excitation voltage is desirably set at 50% of the diaphragm's DC snap-down voltage. For this calculation, the counter electrode is assumed to be rigid. The excitation voltage moves the diaphragm a few percent of the capacitor gap toward the counter electrode. The DC snap-down voltage is calculated according to:

$$V_{snap} = \sqrt{\frac{8k_{cen}g_s^3}{27L_DbF_{sd}\varepsilon}} \quad \text{Eq. 6}$$

The thermal expansion coefficients for polymers are typically $20\times10^{-6}$/° C. for polymers compared to the 0.01 strain/layer assumed for the unrestrained coating plus analyte. These numbers suggest 0.002 layer/° C. thermal sensitivity.

The relationships between diaphragm length and thickness and (i) the resolvable fraction of an analyte molecular layer, (ii) the maximum deflection from baseline due to 1 atmosphere pressure across diaphragm 110, (iii) the excitation voltage as limited by snap-down for the baseline case (see below), and (iv) analyte-induced deflection are illustrated in FIGS. 4-7, respectively. As the diaphragm is made thinner or longer, the snap-down voltage decreases so that the changes in resolution are small and are roughly proportional to the quanitity $\approx \sqrt{L_D h_{Si}}$. As plotted in FIG. 6, the snap-down voltage is proportional to the $L_D^2 h_{Si}^{3/2}$ (diaphragm length and thickness) so that the excitation voltage varies widely. The excitation voltage is a principal consideration in selecting diaphragm dimensions.

Although the present invention has been described with reference to specific details, it is not intended that such details should be regarded as limitations upon the scope of the invention, except as and to the extent that they are included in the accompanying claims.

What is claimed is:

1. A method of detecting binding to or reaction with a selective material, the method comprising the steps of:
   a. providing a sensor comprising:
      i. a diaphragm comprising a conductive portion, a first face, and a second face;
      ii. a selective coating on the first face of the diaphragm;
      iii. a counterelectrode spaced from and in opposition to the diaphragm; and
      iv. perforations through the counterelectrode for equalizing a pressure on each of the first and second faces of the diaphragm,
      wherein the diaphragm is configured to deform upon interaction of the selective coating with an analyte and thereby alter a capacitance of the sensor; and
   b. measuring the capacitance of the sensor to determine a degree of interaction between the analyte and the selective coating.

2. The method of claim 1 wherein the entire diaphragm is conductive.

3. The method of claim 1 wherein the diaphragm is compositionally uniform.

4. The method of claim 1 wherein the measurement step comprises comparing the sensor capacitance to a reference capacitance.

5. The method of claim 4 wherein the reference capacitance is equal to a capacitance of the sensor in the absence of interaction with the selective coating.

6. The method of claim 1 wherein the selective coating comprises a polypeptide.

7. The method of claim 6 wherein the selective coating comprises an antibody.

8. The method of claim 1 wherein the selective coating comprises an antigen.

9. The method of claim 1 further comprising the step of exposing at least the selective coating to a fluid, the measurement step indicating whether an analyte that binds to the coating is present in the fluid.

10. The method of claim 9 wherein the fluid comprises a gas.

11. The method of claim 9 wherein the fluid comprises a liquid.

12. The method of claim 1 wherein the deformation is proportional to a binding energy, which indicates a degree of binding.

13. A sensor comprising:
   a. a diaphragm comprising a conductive portion, a first face, and a second face;
   b. a selective coating on the first face of the diaphragm;
   c. a counterelectrode spaced from and in opposition to the diaphragm; and
   d. perforations through the counterelectrode for equalizing a pressure on each of the first and second faces of the diaphragm,
   wherein the diaphragm is configured to deform upon interaction of the selective coating with an analyte and thereby alter a capacitance of the sensor so as to indicate a degree of interaction.

14. The sensor of claim 13 wherein the entire diaphragm is conductive.

15. The sensor of claim 13 wherein the diaphragm is compositionally uniform.

16. The sensor of claim 13 wherein the selective coating covers only a portion of the first face of the diaphragm.

17. The sensor of claim 13 wherein the coating covers a central half of the first face of the diaphragm.

18. The sensor of claim 13 further comprising circuitry for reporting presence of the analyte.

19. The sensor of claim 13 further comprising circuitry for reporting a concentration of the analyte.

* * * * *